(12) United States Patent
Persson et al.

(10) Patent No.: US 7,419,803 B2
(45) Date of Patent: Sep. 2, 2008

(54) NUCLEIC ACIDS ENCODING HUMAN COAGULATION FACTOR VII POLYPEPTIDES

(75) Inventors: Egon Persson, Malmo (SE); Ole Hvilsted Olsen, Brønshøj (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/088,472

(22) Filed: Mar. 24, 2005

(65) Prior Publication Data
US 2006/0166915 A1 Jul. 27, 2006

Related U.S. Application Data

(63) Continuation of application No. 10/281,727, filed on Oct. 28, 2002, now Pat. No. 6,960,657.

(60) Provisional application No. 60/335,383, filed on Nov. 15, 2001.

(30) Foreign Application Priority Data
Nov. 2, 2001 (DK) ............................... 2001 01627

(51) Int. Cl.
*C12P 21/06* (2006.01)
(52) U.S. Cl. ..................... 435/69.1; 435/6; 435/320.1; 435/252; 435/325; 530/350
(58) Field of Classification Search .............. None
See application file for complete search history.

(56) References Cited

U.S. PATENT DOCUMENTS

| 5,288,629 | A | 2/1994 | Berkner |
|---|---|---|---|
| 5,580,560 | A | 12/1996 | Nicolaisen et al. |
| 5,874,407 | A | 2/1999 | Kelley et al. |
| 5,994,296 | A | 11/1999 | Ruf et al. |
| 2003/0096338 | A1 | 5/2003 | Pedersen et al. |
| 2003/0130191 | A1 | 7/2003 | Persson et al. |
| 2003/0170863 | A1 | 9/2003 | Persson et al. |

FOREIGN PATENT DOCUMENTS

| EP | 0 200 421 B1 | 12/1986 |
|---|---|---|
| JP | 10/59866 A | 3/1998 |
| JP | 2001 061479 | 8/1999 |
| WO | 88/10295 | 6/1987 |
| WO | 94/07515 | 10/1992 |
| WO | 94/27631 | 5/1994 |
| WO | WO 96/12800 | 5/1996 |
| WO | 97/20939 | 11/1996 |
| WO | 98/31394 | 1/1998 |
| WO | 01/58935 A2 | 8/2001 |
| WO | 01/75086 A2 | 10/2001 |
| WO | 01/82943 A2 | 11/2001 |
| WO | 01/83725 A1 | 11/2001 |
| WO | 01/85198 A1 | 11/2001 |
| WO | 02/22776 A2 | 3/2002 |
| WO | 02/38162 A1 | 5/2002 |
| WO | 02/062376 A1 | 8/2002 |
| WO | 02/077218 A1 | 10/2002 |
| WO | 03/027147 A2 | 4/2003 |

OTHER PUBLICATIONS

U.S. Appl. No. 60/184,036, filed Feb. 22, 2000.
Neuenschwander et al., Biochemistry, vol. 34, pp. 8701-8707 (1995).
Bernardi et al., Human Mutation, vol. 8, pp. 108-115 (1996).
Chang et al., Biochemistry, vol. 38, pp. 10940-10948 (1999).
Leonard et al., Abstract 1474, Journ of Int Soc Thromb and Haemost., p. 466 (Suppl. Aug. 1999).
Iakhiev et al., Thromb and Haemost, vol. 85 (3), pp. 458-463 (2001).
Persson et al., Journ of Biol Chem, vol. 276 (31), pp. 29195-29199 (2001).
International Search Report (Aug. 25, 2003).
International Search Report (Feb. 5, 2004).
Peyvandi et al., Throm Haemost, vol. 84, pp. 250-257 (2000).
Peyvandi et al., Throm Haemost, vol. 88, pp. 750-755 (2002).
Soejima et al., Jorun of Bio Chem, vol. 276 (20), pp. 17229-17235 (2001).
U.S. Appl. No. 10/415,963, filed May 5, 2003, Ruf et al.
Dickinson et al., Proc. Natl Acad Sci USA, vol. 93, pp. 14379-14384 (1996).
Abstract of Mizuguchi et al., Journal of the International Society on Thrombosis and Haemostasis, p. 466 (Supplement 1999).
Jianping Jin, Ph.D., UMI Dissertation Services,pp. ii-114 (1999).
Abstract of Kumar A. Fair, D.S., European Journal of Biochemistry (Germany), vol. 217, No. 2, pp. 509-518 (1993).
Stenesh, J., Dict of Biochem and Molec Bio 2$^{nd}$ Ed., p. 97 (Oct. 18, 1989).

*Primary Examiner*—Hope A Robinson
(74) *Attorney, Agent, or Firm*—Reza Green

(57) ABSTRACT

The present invention relates to novel human coagulation Factor VIIa variants having coagulant activity as well as polynucleotide constructs encoding such variants, vectors and host cells comprising and expressing the polynucleotide, pharmaceutical compositions, uses and methods of treatment.

15 Claims, 2 Drawing Sheets

FIGURE 1 - the amino acid sequence of native human coagulation Factor VII

```
Ala-Asn-Ala-Phe-Leu-GLA-GLA-Leu-Arg-Pro-Gly-Ser-Leu-GLA-Arg-GLA-Cys-Lys-
              5                   10                  15

GLA-GLA-Gln-Cys-Ser-Phe-GLA-GLA-Ala-Arg-GLA-Ile-Phe-Lys-Asp-Ala-GLA-Arg-
    20                  25                  30                  35

Thr-Lys-Leu-Phe-Trp-Ile-Ser-Tyr-Ser-Asp-Gly-Asp-Gln-Cys-Ala-Ser-Ser-Pro-
            40                  45                  50

Cys-Gln-Asn-Gly-Gly-Ser-Cys-Lys-Asp-Gln-Leu-Gln-Ser-Tyr-Ile-Cys-Phe-Cys-
 55                  60                  65                  70

Leu-Pro-Ala-Phe-Glu-Gly-Arg-Asn-Cys-Glu-Thr-His-Lys-Asp-Asp-Gln-Leu-Ile-
            75                  80                  85                  90

Cys-Val-Asn-Glu-Asn-Gly-Gly-Cys-Glu-Gln-Tyr-Cys-Ser-Asp-His-Thr-Gly-Thr-
                95                  100                 105

Lys-Arg-Ser-Cys-Arg-Cys-His-Glu-Gly-Tyr-Ser-Leu-Leu-Ala-Asp-Gly-Val-Ser-
        110                 115                 120                 125

Cys-Thr-Pro-Thr-Val-Glu-Tyr-Pro-Cys-Gly-Lys-Ile-Pro-Ile-Leu-Glu-Lys-Arg-
            130                 135                 140

Asn-Ala-Ser-Lys-Pro-Gln-Gly-Arg-Ile-Val-Gly-Gly-Lys-Val-Cys-Pro-Lys-Gly-
145                 150                 155                 160

Glu-Cys-Pro-Trp-Gln-Val-Leu-Leu-Leu-Val-Asn-Gly-Ala-Gln-Leu-Cys-Gly-Gly-
        165                 170                 175                 180

Thr-Leu-Ile-Asn-Thr-Ile-Trp-Val-Val-Ser-Ala-Ala-His-Cys-Phe-Asp-Lys-Ile-
                185                 190                 195
```

Fig. 1

```
Lys-Asn-Trp-Arg-Asn-Leu-Ile-Ala-Val-Leu-Gly-Glu-His-Asp-Leu-Ser-Glu-His-
200              205              210              215

Asp-Gly-Asp-Glu-Gln-Ser-Arg-Arg-Val-Ala-Gln-Val-Ile-Ile-Pro-Ser-Thr-Tyr-
         220              225              230

Val-Pro-Gly-Thr-Thr-Asn-His-Asp-Ile-Ala-Leu-Leu-Arg-Leu-His-Gln-Pro-Val-
235              240              245              250

Val-Leu-Thr-Asp-His-Val-Val-Pro-Leu-Cys-Leu-Pro-Glu-Arg-Thr-Phe-Ser-Glu-
         255              260              265              270

Arg-Thr-Leu-Ala-Phe-Val-Arg-Phe-Ser-Leu-Val-Ser-Gly-Trp-Gly-Gln-Leu-Leu-
         275              280              285

Asp-Arg-Gly-Ala-Thr-Ala-Leu-Glu-Leu-Met-Val-Leu-Asn-Val-Pro-Arg-Leu-Met-
290              295              300              305 306

Thr-Gln-Asp-Cys-Leu-Gln-Gln-Ser-Arg-Lys-Val-Gly-Asp-Ser-Pro-Asn-Ile-Thr-
         310              315              320

Glu-Tyr-Met-Phe-Cys-Ala-Gly-Tyr-Ser-Asp-Gly-Ser-Lys-Asp-Ser-Cys-Lys-Gly-
325              330              335              340

Asp-Ser-Gly-Gly-Pro-His-Ala-Thr-His-Tyr-Arg-Gly-Thr-Trp-Tyr-Leu-Thr-Gly-
         345              350              355              360

Ile-Val-Ser-Trp-Gly-Gln-Gly-Cys-Ala-Thr-Val-Gly-His-Phe-Gly-Val-Tyr-Thr-
         365              370              375

Arg-Val-Ser-Gln-Tyr-Ile-Glu-Trp-Leu-Gln-Lys-Leu-Met-Arg-Ser-Glu-Pro-Arg-
380              385              390              395

Pro-Gly-Val-Leu-Leu-Arg-Ala-Pro-Phe-Pro
         400              405 406
```

Fig. 1 (continued)

NUCLEIC ACIDS ENCODING HUMAN COAGULATION FACTOR VII POLYPEPTIDES

CROSS REFERENCE TO RELATED APPLICATIONS

This application is a continuation of Ser. No. 10/281,727 filed Oct. 28, 2002 issued as U.S. Pat. No. 6,960,657, and claims the benefit of priority under 35 U.S.C. 119 of Danish application no. PA 2001 01627 filed on Nov. 2, 2001 and U.S. provisional application No. 60/335,383 filed on Nov. 15, 2001, the contents of which are fully incorporated herein by reference.

FIELD OF THE INVENTION

The present invention relates to novel human coagulation Factor VII polypeptides having coagulant activity as well as polynucleotide constructs encoding such polypeptides, vectors and host cells comprising and expressing the polynucleotide, pharmaceutical compositions, uses and methods of treatment.

BACKGROUND OF THE INVENTION

Blood coagulation is a process consisting of a complex interaction of various blood components (or factors) that eventually gives raise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa).

Initiation of the haemostatic process is mediated by the formation of a complex between tissue factor, exposed as a result of injury to the vessel wall, and Factor VIIa. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot. In recent years Factor VII and tissue factor have been found to be the main initiators of blood coagulation.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. Like several other plasma proteins involved in haemostasis, Factor VII is dependent on Vitamin K for its activity, which is required for the gamma-carboxylation of multiple glutamic acid residues that are clustered close to the amino terminus of the protein. These gamma-carboxylated glutamic acids are required for the metal ion-induced interaction of Factor VII with phospholipids. The conversion of zymogen Factor VII into the activated two-chain molecule occurs by cleavage of an internal $Arg_{152}$-$Ile_{153}$ peptide bond. In the presence of tissue factor, phospholipids and calcium ions, the two-chain Factor VIIa rapidly activates Factor X or Factor IX by limited proteolysis.

It is often desirable to stimulate or improve the coagulation cascade in a subject. Factor VIIa has been used to control bleeding disorders that have several causes such as clotting factor deficiencies (e.g. haemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease. Bleeding is also a major problem in connection with surgery and other forms of tissue damage.

European Patent No. 200,421 (ZymoGenetics) relates to the nucleotide sequence encoding human Factor VII and the recombinant expression of Factor VII in mammalian cells.

Dickinson et al. (Proc. Natl. Acad. Sci. USA (1996) 93, 14379-14384) relates to a Factor VII variant wherein Leu305 has been replaced by Ala (FVII(Ala305)).

Iwanaga et al. (Thromb. Haemost. (supplement Aug. 1999), 466, abstract 1474) relates to Factor VIIa variants wherein residues 316-320 are deleted or residues 311-322 are replaced with the corresponding residues from trypsin.

There is a need for variants of Factor VIIa having coagulant activity, variants with high activity that can be administered at relatively low doses, and variants which do not produce the undesirable side effects such as systemic activation of the coagulation system and bleeding, respectively, associated with conventional therapies.

BRIEF DESCRIPTION OF THE DRAWINGS

FIG. 1 shows the full amino acid sequence of native (wild type) human coagulation Factor. VII (SEQ ID NO:1).

DESCRIPTION OF THE INVENTION

It has now been found that human coagulation Factor VIIa polypeptide variants with mutations in the loop comprising amino acid residues 313-329 of SEQ ID NO:1 (e.g. Ser314 and Lys316) and at positions outside this range, but spatially proximal to this loop (e.g. Trp364, Gln366, His373, and Val376) have increased activity compared to wild-type Factor VIIa. These positions include.

The term "activity" as used herein means the ability of a Factor VII polypeptide to convert its substrate Factor X to the active Factor Xa. The activity of a Factor VII polypeptide may be measured with the "In Vitro Proteolysis Assay" (see Example 5).

The term "inherent activity" also includes the ability to generate thrombin on the surface of activated platelets in the absence of tissue factor.

Due to the higher inherent activity of the described Factor VIIa polypeptide variants compared to native FVIIa, a lower dose may be adequate to obtain a functionally adequate concentration at the site of action and thus it will be possible to administer a lower dose to the subject having bleeding episodes or needing enhancement of the normal haemostatic system.

It has been found by the present inventors that by replacing the amino acids in the loop comprising amino acid residues 313-329 of SEQ ID NO:1, e.g. Ser314 or Lys316 and at position outside this range, but spatially proximal to this loop, e.g. Trp364, Gln366, His373, and Val376, Factor VIIa will spontaneously attain a more active conformation that normally has to be induced by tissue factor. Such Factor VIIa polypeptide variants exhibit an inherent activity which may be therapeutically useful in situations where the procoagulant activity is independent of tissue factor (Factor Xa generation on the platelet surface) such as when high doses of, for example, NOVOSEVEN® are administered.

In one embodiment additional replacement of amino acids in the protease domain further facilitate formation of the active conformation of the molecule. In one embodiment the Factor VIIa polypeptide further comprises replacement with any other amino acid of one or more amino acids selected from the group consisting of amino acids Leu305, Lys157, Lys337, Asp334, Ser336, Val158, Glu296, and Met298.

The invention further comprises replacement of a few amino acids in the N-terminal Gla domain (amino acids at position corresponding to 1-37 of SEQ ID NO:1) of Factor VIIa can provide the protein with a substantially higher affinity for membrane phospholipids, such as membrane phospholipids of tissue factor-bearing cells or of platelets, thereby generating Factor VII polypeptide variants which have an improved procoagulant effect.

Thus, the Factor VIIa polypeptide variants mentioned above may, in addition to the already performed amino acid replacement in position 313-329 of SEQ ID NO:1 and the optional amino acid replacements elsewhere in the protease domain, also have at least one amino acid replaced in the N-terminal Gla domain, thereby obtaining a protein having an increased activity as well as an increased affinity for membrane phospholipids compared to native Factor VIIa. Preferably the amino acids in positions 10 and 32 (referring to SEQ ID NO:1) of Factor VIIa may be replaced with a different amino acid. Examples of preferred amino acids to be incorporated in the above-mentioned positions are: The amino acid Pro in position 10 is replaced by Gln, Arg, His, Gln, Asn or Lys; and/or the amino acid Lys in position 32 is replaced by Glu, Gln or Asn.

Other amino acids in the Gla domain, based on the different phospholipid affinities and sequences of the vitamin K-dependent plasma proteins, may also be considered for substitution.

The term "N-terminal GLA-domain" means the amino acid sequence 1-37 of Factor VII.

The three-letter indication "GLA" means 4-carboxyglutamic acid (γ-carboxyglutamate).

The term "protease domain" means the amino acid sequence 153-406 of Factor VII (the heavy-chain of Factor VIIa).

The term "Factor VII polypeptide" as used herein means any protein comprising the amino acid sequence 1-406 of native human Factor VII (SEQ ID NO:1) or variants thereof. This includes but are not limited to human Factor VII, human Factor VIIa and variants thereof.

The term "Factor VII" as used herein is intended to comprise the inactive one-chain zymogen Factor VII molecule as well as the activated two-chain Factor VII molecule (Factor VIIa). This includes proteins that have the amino acid sequence 1-406 of native human Factor VII or Factor VIIa. It also includes proteins with a slightly modified amino acid sequence, for instance, a modified N-terminal end including N-terminal amino acid deletions or additions so long as those proteins substantially retain the activity of Factor VIIa. The term "factor VIIa", or "FVIIa" as used herein means a product consisting of the activated form (factor VIIa). "Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

The terms "variant" or "variants", as used herein, is intended to designate Factor VII having the sequence of SEQ ID NO:1, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "variant" or "variants" within this definition still have FVII activity in its activated form. In one embodiment a variant is 70% identical with the sequence of SEQ ID NO:1. In one embodiment a variant is 80% identical with the sequence of SEQ ID NO:1. In another embodiment a variant is 90% identical with the sequence of SEQ ID NO:1. In a further embodiment a variant is 95% identical with the sequence of SEQ ID NO:1.

In a first aspect, the invention relates to a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329 of SEQ ID NO:1 or any other amino acid in spatial proximity.

The term "any other amino acid" as used herein means one amino acid that are different from that amino acid naturally present at that position. This includes but are not limited to amino acids that can be encoded by a polynucleotide. Preferably the different amino acid is in natural L-form and can be encoded by a polynucleotide. A specific example being L-cysteine (Cys).

In a second aspect, the invention relates to a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329 of SEQ ID NO:1.

In a third aspect, the invention relates to a Factor VII polypeptide comprising at least one amino acid substitution relative to the amino acid sequence of SEQ ID NO:1, wherein said substitution is replacement with any other amino acid of one or more amino acids selected from the group consisting of amino acids 313-329, 364, 366, 373, and 376 of SEQ ID NO:1.

In a further aspect, the invention relates to a Factor VII polypeptide with one amino acid substitution relative to the amino acid sequence of SEQ ID NO:1, wherein the substitution is replacement with any other amino acid of one amino acid selected from the group consisting of amino acids 313-329, 364, 366, 373, and 376 of SEQ ID NO:1.

In a further aspect, the invention relates to a Factor VII polypeptide with two amino acid substitutions relative to the amino acid sequence of SEQ ID NO:1, wherein the substitutions are replacements with any other amino acids of two amino acids selected from the group consisting of amino acids 313-329, 364, 366, 373, and 376 of SEQ ID NO:1.

In a further aspect, the invention relates to a Factor VII polypeptide with three amino acid substitutions relative to the amino acid sequence of SEQ ID NO:1, wherein the substitutions are replacements with any other amino acids of three amino acids selected from the group consisting of amino acids 313-329, 364, 366, 373, and 376 of SEQ ID NO:1.

In a further aspect, the invention relates to a Factor VII polypeptide with four amino acid substitutions relative to the amino acid sequence of SEQ ID NO:1, wherein the substitutions are replacements with any other amino acids of four amino acids selected from the group consisting of amino acids 313-329, 364, 366, 373, and 376 of SEQ ID NO:1.

In a further aspect, the invention relates to a Factor VII polypeptide with one amino acid substitution relative to the amino acid sequence of SEQ ID NO:1, wherein the substitution is replacement with any other amino acid of one amino acid selected from the group consisting of amino acids 313-329 of SEQ ID NO:1.

In a further aspect, the invention relates to a Factor VII polypeptide with two amino acid substitutions relative to the amino acid sequence of SEQ ID NO:1, wherein the substitutions are replacements with any other amino acids of two amino acids selected from the group consisting of amino acids 313-329 of SEQ ID NO:1.

In a further aspect, the invention relates to a Factor VII polypeptide with three amino acid substitutions relative to the amino acid sequence of SEQ ID NO:1, wherein the substitutions are replacements with any other amino acids of three amino acids selected from the group consisting of amino acids 313-329 of SEQ ID NO:1.

In a further aspect, the invention relates to a Factor VII polypeptide with four amino acid substitutions relative to the amino acid sequence of SEQ ID NO:1, wherein the substitutions are replacements with any other amino acids of four amino acids selected from the group consisting of amino acids 313-329 of SEQ ID NO:1.

In a further aspect, the invention relates to a polynucleotide construct encoding a Factor VII polypeptide of the invention.

The term "construct" is intended to indicate a polynucleotide segment which may be based on a complete or partial naturally occurring nucleotide sequence encoding the polypeptide of interest. The construct may optionally contain other polynucleotide segments. In a similar way, the term "amino acids which can be encoded by polynucleotide constructs" covers amino acids which can be encoded by the polynucleotide constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

In a further aspect, the invention provides a recombinant vector comprising the polynucleotide construct encoding a Factor VII polypeptide of the invention.

The term "vector", as used herein, means any nucleic acid entity capable of the amplification in a host cell. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contains a replication origin and at least one selectable gene, i.e., a gene which encodes a product which is readily detectable or the presence of which is essential for cell growth.

In a further aspect, the invention provides a recombinant host cell comprising the polynucleotide construct or the vector. In one embodiment the recombinant host cell is a eukaryotic cell. In another embodiment the recombinant host cell is of mammalian origin. In a further embodiment the recombinant host cell is selected from the group consisting of CHO cells, HEK cells and BHK cells.

The term "a host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 10801 University, Boulevard, Manassas, Va. 20110, under ATCC accession number CRL 10314. A tk-ts13 BHK cell line is also available from the ATCC under accession number CRL 1632. Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216-4220, 1980). Also useful are 3T3 cells, Namalwa cells, myelomas and fusions of myelomas with other cells.

In a further aspect, the invention provides a transgenic animal containing and expressing the polynucleotide construct.

In a further aspect, the invention provides a transgenic plant containing and expressing the polynucleotide construct.

In a further aspect, the invention relates to a method for producing the Factor VII polypeptide of the invention, the method comprising cultivating a cell comprising the polynucleotide construct in an appropriate growth medium under conditions allowing expression of the polynucleotide construct and recovering the resulting polypeptide from the culture medium.

As used herein the term "appropriate growth medium" means a medium containing nutrients and other components required for the growth of cells and the expression of the nucleic acid sequence encoding the Factor VII polypeptide of the invention.

In a further aspect, the invention relates to a method for producing the Factor VII polypeptide, the method comprising recovering the polypeptide from milk produced by the transgenic animal.

In a further aspect, the invention relates to a method for producing the Factor VII polypeptide, the method comprising cultivating a cell of a transgenic plant comprising the polynucleotide construct, and recovering the polypeptide from the resulting plant.

In a further aspect, the invention relates to a pharmaceutical composition comprising a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329, 364, 366, 373, and 376 of SEQ ID NO:1 or any other amino acid in spatial proximity; and, optionally, a pharmaceutically acceptable carrier.

In a further aspect, the invention relates to a pharmaceutical composition comprising a Factor VII polypeptide comprising at least one amino acid substitution relative to the amino acid sequence of SEQ ID NO:1, wherein the substitution is replacement with any other amino acid of one or more amino acids selected from the group consisting of amino acids 313-

329 of SEQ ID NO:1 or any other amino acid in spatial proximity; and, optionally, a pharmaceutically acceptable carrier.

In a further aspect, the invention relates to the use of a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329, 364, 366, 373, and 376 of SEQ ID NO:1 or any other amino acid in spatial proximity; for the preparation of a medicament for the treatment of bleeding disorders or bleeding episodes or for the enhancement of the normal haemostatic system.

In a further aspect, the invention relates to the use of a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329 of SEQ ID NO:1 or any other amino acid in spatial proximity; for the preparation of a medicament for the treatment of bleeding disorders or bleeding episodes or for the enhancement of the normal haemostatic system.

In one embodiment the use is for the treatment of haemophilia A or B.

In the present context, the term "treatment" is meant to include both prevention of an expected bleeding, such as in surgery, and regulation of an already occurring bleeding, such as in trauma, with the purpose of inhibiting or minimising the bleeding. Prophylactic administration of the Factor VIIa polypeptide according to the invention is thus included in the term "treatment".

The term "bleeding episodes" is meant to include uncontrolled and excessive bleeding. Bleeding episodes may be a major problem both in connection with surgery and other forms of tissue damage. Uncontrolled and excessive bleeding may occur in subjects having a normal coagulation system and subjects having coagulation or bleeding disorders. As used herein the term "bleeding disorder" reflects any defect, congenital, acquired or induced, of cellular or molecular origin that is manifested in bleedings. Examples are clotting factor deficiencies (e.g. haemophilia A and B or deficiency of coagulation Factors XI or VII), clotting factor inhibitors, defective platelet function, thrombocytopenia or von Willebrand's disease.

Excessive bleedings also occur in subjects with a normally functioning blood clotting cascade (no clotting factor deficiencies or -inhibitors against any of the coagulation factors) and may be caused by a defective platelet function, thrombocytopenia or von Willebrand's disease. In such cases, the bleedings may be likened to those bleedings caused by haemophilia because the haemostatic system, as in haemophilia, lacks or has abnormal essential clotting "compounds" (such as platelets or von Willebrand factor protein) that causes major bleedings. In subjects who experience extensive tissue damage in association with surgery or vast trauma, the normal haemostatic mechanism may be overwhelmed by the demand of immediate haemostasis and they may develop bleeding in spite of a normal haemostatic mechanism. Achieving satisfactory haemostasis also is a problem when bleedings occur in organs such as the brain, inner ear region and eyes with limited possibility for surgical haemostasis. The same problem may arise in the process of taking biopsies from various organs (liver, lung, tumour tissue, gastrointestinal tract) as well as in laparoscopic surgery. Common for all these situations is the difficulty to provide haemostasis by surgical techniques (sutures, clips, etc.) which also is the case when bleeding is diffuse (haemorrhagic gastritis and profuse uterine bleeding). Acute and profuse bleedings may also occur in subjects on anticoagulant therapy in whom a defective haemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical haemostasis, and which may result in diffuse bleeding from a large area. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with haemophilia. In another embodiment, the bleeding is associated with haemophilia with aquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with haemorrhagic gastritis. In another embodiment, the bleeding is profuse uterine bleeding. In another embodiment, the bleeding is occurring in organs with a limited possibility for mechanical haemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The term "subject" as used herein is intended to mean any animal, in particular mammals, such as humans, and may, where appropriate, be used interchangeably with the term "patient".

The term "enhancement of the normal haemostatic system" means an enhancement of the ability to generate thrombin.

In a further aspect, the invention relates to the Factor VII polypeptide of the invention for use as a medicament.

In a further aspect, the invention relates to a method for the treatment of bleeding disorders or bleeding episodes in a subject or for the enhancement of the normal haemostatic system, the method comprising administering a therapeutically or prophylactically effective amount of a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329, 364, 366, 373, and 376 of SEQ ID NO:1 or any other amino acid in spatial proximity; to a subject in need thereof.

In a further aspect, the invention relates to a method for the treatment of bleeding disorders or bleeding episodes in a subject or for the enhancement of the normal haemostatic system, the method comprising administering a therapeutically or prophylactically effective amount of a Factor VII polypeptide comprising at least one amino acid substitution relative to the amino acid sequence of SEQ ID NO:1, wherein the substitution is replacement with any other amino acid of one or more amino acids selected from the group consisting of amino acids 313-329 of SEQ ID NO:1 or any other amino acid in spatial proximity; to a subject in need thereof.

In one embodiment of the invention, the factor VII polypeptide is a polypeptide, wherein Q313 is replaced with any other amino acid.

In one embodiment of the invention, the factor VII polypeptide is a polypeptide, wherein R315 is replaced with any other amino acid.

In one embodiment of the invention, the factor VII polypeptide is a polypeptide, wherein V317 is replaced with any other amino acid.

In one embodiment of the invention, the factor VII polypeptide is a polypeptide, wherein G318 is replaced with any other amino acid.

In one embodiment of the invention, the factor VII polypeptide is a polypeptide, wherein D319 is replaced with any other amino acid.

In one embodiment of the invention, the factor VII polypeptide is a polypeptide, wherein S320 is replaced with any other amino acid.

In one embodiment of the invention, the factor VII polypeptide is a polypeptide, wherein P321 is replaced with any other amino acid.

In one embodiment of the invention, the factor VII polypeptide is a polypeptide, wherein N322 is replaced with any other amino acid.

In one embodiment of the invention, the factor VII polypeptide is a polypeptide, wherein I323 is replaced with any other amino acid.

In one embodiment of the invention, the factor VII polypeptide is a polypeptide, wherein T324 is replaced with any other amino acid.

In one embodiment of the invention, the factor VII polypeptide is a polypeptide, wherein E325 is replaced with any other amino acid.

In one embodiment of the invention, the factor VII polypeptide is a polypeptide, wherein Y326 is replaced with any other amino acid.

In one embodiment of the invention, the factor VII polypeptide is a polypeptide, wherein M327 is replaced with any other amino acid.

In one embodiment of the invention, the factor VII polypeptide is a polypeptide, wherein F328 is replaced with any other amino acid.

In one embodiment of the invention, the factor VII polypeptide is a polypeptide, wherein C329 is replaced with any other amino acid.

In one embodiment of the invention, the factor VII polypeptide is a polypeptide, wherein S314 is replaced with any other amino acid.

In a further embodiment of the invention, the factor VII polypeptide is a polypeptide, wherein K316 is replaced with any other amino acid.

In a further embodiment of the invention, the factor VII polypeptide is a polypeptide, wherein W364 is replaced with any other amino acid.

In a further embodiment of the invention, the factor VII polypeptide is a polypeptide, wherein Q366 is replaced with any other amino acid.

In a further embodiment of the invention, the factor VII polypeptide is a polypeptide, wherein H373 is replaced with any other amino acid.

In a further embodiment of the invention, the factor VII polypeptide is a polypeptide, wherein V376 is replaced with any other amino acid.

In a further embodiment of the invention, the factor VII polypeptide is a polypeptide, wherein L305 is further replaced with any other amino acid.

In a further embodiment of the invention, the factor VII polypeptide is a polypeptide, wherein K157 is further replaced with any other amino acid.

In a further embodiment of the invention, the factor VII polypeptide is a polypeptide, wherein K337 is further replaced with any other amino acid.

In a further embodiment of the invention, the factor VII polypeptide is a polypeptide, wherein D334 is further replaced with any other amino acid.

In a further embodiment of the invention, the factor VII polypeptide is a polypeptide, wherein S336 is further replaced with any other amino acid.

In a further embodiment of the invention, the factor VII polypeptide is a polypeptide, wherein V158 is further replaced with any other amino acid.

In a further embodiment of the invention, the factor VII polypeptide is a polypeptide, wherein E296 is further replaced with any other amino acid.

In a further embodiment of the invention, the factor VII polypeptide is a polypeptide, wherein M298 is further replaced with any other amino acid.

In a further embodiment of the invention, the factor VII polypeptide is a polypeptide, wherein at least one amino acid in the remaining positions in the protease domain has been replaced with any other amino acid.

In a further embodiment of the invention, the factor VII polypeptide is a polypeptide, wherein at the most 20 additional amino acids in the remaining positions in the protease domain have been replaced with any other amino acids.

In a further embodiment of the invention, the factor VII polypeptide is a polypeptide, wherein at least one amino acid corresponding to an amino acid at a position selected from 159-170 of SEQ ID NO:1 has been replaced with any other amino acid.

In a further embodiment of the invention, the factor VII polypeptide is a polypeptide, wherein at least one amino acid corresponding to an amino acid at a position selected from 290-304 of SEQ ID NO:1 has been replaced with any other amino acid.

In a further embodiment of the invention, the factor VII polypeptide is a polypeptide, wherein R304 has been replaced by an amino acid selected from the group consisting of Tyr, Phe, Leu, and Met.

In a further embodiment of the invention, the factor VII polypeptide is a polypeptide, wherein at least one amino acid corresponding to an amino acid at a position selected from 306-312 of SEQ ID NO:1 has been replaced with any other amino acid.

In a further embodiment of the invention, the factor VII polypeptide is a polypeptide, wherein M306 has been replaced by an amino acid selected from the group consisting of Asp, and Asn.

In a further embodiment of the invention, the factor VII polypeptide is a polypeptide, wherein D309 has been replaced by an amino acid selected from the group consisting of Ser, and Thr.

In a further embodiment of the invention, the factor VII polypeptide is a polypeptide, wherein at least one amino acid corresponding to an amino acid at a position selected from 330-339 of SEQ ID NO:1 has been replaced with any other amino acid.

In a further embodiment of the invention, the factor VII polypeptide is a polypeptide, wherein A274 has been replaced with any other amino acid.

In a further embodiment of the invention, the factor VII polypeptide is a polypeptide, wherein the A274 has been replaced by an amino acid selected from the group consisting of Met, Leu, Lys, and Arg.

In a further embodiment of the invention, the factor VII polypeptide is a polypeptide, wherein the S314 has been replaced by an amino acid selected from the group consisting of Gly, and Glu.

In a further embodiment of the invention, the factor VII polypeptide is a polypeptide, wherein the wherein K316 has been replaced by an amino acid selected from the group consisting of Gly, His, Val, Ser, Thr, Asn, Gln, Asp, and Glu.

In a further embodiment of the invention, the factor VII polypeptide is a polypeptide, wherein the S314 has been replaced by Glu.

In a further embodiment of the invention, the factor VII polypeptide is a polypeptide, wherein the K316 has been replaced by Gln.

In a further embodiment of the invention, the factor VII polypeptide is a polypeptide, wherein the K157 has been replaced by an amino acid selected from the group consisting of Gly, Val, Ser, Thr, Asn, Gln, Asp, and Glu.

In a further embodiment of the invention, the factor VII polypeptide is a polypeptide, wherein the K337 has been replaced by an amino acid selected from the group consisting of Ala, Gly, Val, Ser, Thr, Asn, Gln, Asp, and Glu.

In a further embodiment of the invention, the factor VII polypeptide is a polypeptide, wherein the D334 has been replaced by an amino acid selected from the group consisting of Gly, and Glu.

In a further embodiment of the invention, the factor VII polypeptide is a polypeptide, wherein the S336 has been replaced by an amino acid selected from the group consisting of Gly, and Glu.

In a further embodiment of the invention, the factor VII polypeptide is a polypeptide, wherein the V158 has been replaced by an amino acid selected from the group consisting of Ser, Thr, Asn, Gln, Asp, and Glu.

In a further embodiment of the invention, the factor VII polypeptide is a polypeptide, wherein the E296 has been replaced by an amino acid selected from the group consisting of Arg, Lys, and Val.

In a further embodiment of the invention, the factor VII polypeptide is a polypeptide, wherein the M298 has been replaced by an amino acid selected from the group consisting of Lys, Arg, Gln, and Asn.

In a further embodiment of the invention, the factor VII polypeptide is a polypeptide, wherein the L305 has been replaced by an amino acid selected from the group consisting of Val, Tyr and Ile.

In a further embodiment of the invention, the factor VII polypeptide is a polypeptide, wherein the L305 has been replaced by Val.

In a further embodiment of the invention, the factor VII polypeptide is a polypeptide, wherein the amino acid has been replaced by a different amino acid which can be encoded by polynucleotide constructs.

In a further embodiment of the invention, the factor VII polypeptide is a polypeptide, wherein the Factor VII polypeptide is human Factor VII.

In a further embodiment of the invention, the factor VII polypeptide is a polypeptide, wherein the Factor VII polypeptide is human Factor VIIa.

In a further embodiment of the invention, the factor VII polypeptide is a polypeptide, wherein the ratio between the activity of the Factor VII polypeptide and the activity of the native Factor VIIa polypeptide shown in SEQ ID NO:1 is at least about 1.25. In one embodiment the ratio between the activity of the Factor VII polypeptide and the activity of the native Factor VIIa polypeptide shown in SEQ ID NO:1 is at least about 2.0. In a further embodiment the ratio between the activity of the Factor VII polypeptide and the activity of the native Factor VIIa polypeptide shown in SEQ ID NO:1 is at least about 4.0.

In a further embodiment of the invention, the factor VII polypeptide is a polypeptide, wherein the ratio between the activity of the Factor VII polypeptide and the activity of the native Factor VIIa polypeptide shown in SEQ ID NO:1 is at least about 1.25 when tested in a Factor VIIa activity assay. In one embodiment the ratio between the activity of the Factor VII polypeptide and the activity of the native Factor VIIa polypeptide shown in SEQ ID NO:1 is at least about 2.0 when tested in a Factor VIIa activity assay. In a further embodiment the ratio between the activity of the Factor VII polypeptide and the activity of the native Factor VIIa polypeptide shown in SEQ ID NO:1 is at least about 4.0 when tested in a Factor VIIa activity assay. The Factor VIIa activity may be measured by the assays described in examples 4 or 5.

In a further embodiment of the invention, the factor VII polypeptide is a polypeptide, wherein the ratio between the activity of the Factor VII polypeptide and the activity of the native Factor VIIa polypeptide shown in SEQ ID NO:1 is at least about 1.25 when tested in the "In Vitro Hydrolysis Assay". In one embodiment the ratio between the activity of the Factor VII polypeptide and the activity of the native Factor VIIa polypeptide shown in SEQ ID NO:1 is at least about 2.0 when tested in the "In Vitro Hydrolysis Assay". In a further embodiment the ratio between the activity of the Factor VII polypeptide and the activity of the native Factor VIIa polypeptide shown in SEQ ID NO:1 is at least about 4.0 when tested in the "In Vitro Hydrolysis Assay".

In a further embodiment of the invention, the factor VII polypeptide is a polypeptide, wherein the ratio between the activity of the Factor VII polypeptide and the activity of the native Factor VIIa polypeptide shown in SEQ ID NO:1 is at least about 1.25 when tested in the "In Vitro Proteolysis Assay". In one embodiment the ratio between the activity of the Factor VII polypeptide and the activity of the native Factor VIIa polypeptide shown in SEQ ID NO:1 is at least about 2.0 when tested in the "In Vitro Proteolysis Assay". In a further embodiment the ratio between the activity of the Factor VII polypeptide and the activity of the native Factor VIIa polypeptide shown in SEQ ID NO:1 is at least about 4.0 when tested in the "In Vitro Proteolysis Assay". In a further embodiment the ratio between the activity of the Factor VII polypeptide and the activity of the native Factor VIIa polypeptide shown in SEQ ID NO:1 is at least about 8.0 when tested in the "In Vitro Proteolysis Assay".

In a further embodiment of the invention, the factor VII polypeptide is human FVII with at least two substitutions relative to the amino acid sequence of SEQ ID NO:1, wherein the substitutions are (i) $S314X^2$ and (ii) one or more amino acids selected from the group consisting of, $K157X^1$, $S316X^1$, K337A, $D334X^2$, $S336X^3$, $V158X^4$, $L305X^5$, E296V, and M298Q, wherein $X^1$ is Gly, His, Val, Ser, Thr, Asn, Gln, Asp, or Glu; $X^2$ is Gly or Glu; $X^3$ is Gly or Glu; $X^4$ is Thr or Asp; $X^5$ is Val, Tyr, or Ile.

In a further embodiment of the invention, the factor VII polypeptide is human FVII with at least two substitutions relative to the amino acid sequence of SEQ ID NO:1, wherein the substitutions are (i) $S316X^1$ and (ii) one or more amino acids selected from the group consisting of, $K157X^1$, $S314X^2$, K337A, $D334X^2$, $S336X^3$, $V158X^4$, $L305X^5$, E296V, and M298Q, wherein $X^1$ is Gly, His, Val, Ser, Thr, Asn, Gln, Asp, or Glu; $X^2$ is Gly or Glu; $X^3$ is Gly or Glu; $X^4$ is Thr or Asp; $X^5$ is Val, Tyr, or Ile.

In a further embodiment of the invention, the factor VII polypeptide is S314E/K316H-FVII.

In a further embodiment of the invention, the factor VII polypeptide is S314E/K316Q-FVII.

In a further embodiment of the invention, the factor VII polypeptide is S314E/L305V-FVII.

In a further embodiment of the invention, the factor VII polypeptide is S314E/K337A-FVII.

In a further embodiment of the invention, the factor VII polypeptide is S314E/V158D-FVII.

In a further embodiment of the invention, the factor VII polypeptide is S314E/E296V-FVII.

In a further embodiment of the invention, the factor VII polypeptide is S314E/M298Q-FVII.

In a further embodiment of the invention, the factor VII polypeptide is S314E/V158T-FVII.

In a further embodiment of the invention, the factor VII polypeptide is K316H/L305V-FVII.

In a further embodiment of the invention, the factor VII polypeptide is K316H/K337A-FVII.

In a further embodiment of the invention, the factor VII polypeptide is K316H/V158D-FVII.

In a further embodiment of the invention, the factor VII polypeptide is K316H/E296V-FVII.

In a further embodiment of the invention, the factor VII polypeptide is K316H/M298Q-FVII.

In a further embodiment of the invention, the factor VII polypeptide is K316H/V158T-FVII.

In a further embodiment of the invention, the factor VII polypeptide is K316Q/L305V-FVII.

In a further embodiment of the invention, the factor VII polypeptide is K316Q/K337A-FVII.

In a further embodiment of the invention, the factor VII polypeptide is K316Q/V158D-FVII.

In a further embodiment of the invention, the factor VII polypeptide is K316Q/E296V-FVII.

In a further embodiment of the invention, the factor VII polypeptide is K316Q/M298Q-FVII.

In a further embodiment of the invention, the factor VII polypeptide is K316Q/V158T-FVII.

In a further embodiment of the invention, the factor VII polypeptide is S314E/L305V/K337A-FVII.

In a further embodiment of the invention, the factor VII polypeptide is S314E/L305V/V158D-FVII.

In a further embodiment of the invention, the factor VII polypeptide is S314E/L305V/E296V-FVII.

In a further embodiment of the invention, the factor VII polypeptide is S314E/L305V/M298Q-FVII.

In a further embodiment of the invention, the factor VII polypeptide is S314E/L305V/V158T-FVII.

In a further embodiment of the invention, the factor VII polypeptide is S314E/L305V/K337A/V158T-FVII.

In a further embodiment of the invention, the factor VII polypeptide is S314E/L305V/K337A/M298Q-FVII.

In a further embodiment of the invention, the factor VII polypeptide is S314E/L305V/K337A/E296V-FVII.

In a further embodiment of the invention, the factor VII polypeptide is S314E/L305V/K337A/V158D-FVII.

In a further embodiment of the invention, the factor VII polypeptide is S314E/L305V/V158D/M298Q-FVII.

In a further embodiment of the invention, the factor VII polypeptide is S314E/L305V/V158D/E296V-FVII.

In a further embodiment of the invention, the factor VII polypeptide is S314E/L305V/V158T/M298Q-FVII.

In a further embodiment of the invention, the factor VII polypeptide is S314E/L305V/V158T/E296V-FVII.

In a further embodiment of the invention, the factor VII polypeptide is S314E/L305V/E296V/M298Q-FVII.

In a further embodiment of the invention, the factor VII polypeptide is S314E/L305V/V158D/E296V/M298Q-FVII.

In a further embodiment of the invention, the factor VII polypeptide is S314E/L305V/V158T/E296V/M298Q-FVII.

In a further embodiment of the invention, the factor VII polypeptide is S314E/L305V/V158T/K337A/M298Q-FVII.

In a further embodiment of the invention, the factor VII polypeptide is S314E/L305V/V158T/E296V/K337A-FVII.

In a further embodiment of the invention, the factor VII polypeptide is S314E/L305V/V158D/K337A/M298Q-FVII.

In a further embodiment of the invention, the factor VII polypeptide is S314E/L305V/V158D/E296V/K337A-FVII.

In a further embodiment of the invention, the factor VII polypeptide is S314E/L305V/V158D/E296V/M298Q/K337A-FVII.

In a further embodiment of the invention, the factor VII polypeptide is S314E/L305V/V158T/E296V/M298Q/K337A-FVII.

In a further embodiment of the invention, the factor VII polypeptide is K316H/L305V/K337A-FVII.

In a further embodiment of the invention, the factor VII polypeptide is K316H/L305V/V158D-FVII.

In a further embodiment of the invention, the factor VII polypeptide is K316H/L305V/E296V-FVII.

In a further embodiment of the invention, the factor VII polypeptide is K316H/L305V/M298Q-FVII.

In a further embodiment of the invention, the factor VII polypeptide is K316H/L305V/V158T-FVII.

In a further embodiment of the invention, the factor VII polypeptide is K316H/L305V/K337A/V158T-FVII.

In a further embodiment of the invention, the factor VII polypeptide is K316H/L305V/K337A/M298Q-FVII.

In a further embodiment of the invention, the factor VII polypeptide is K316H/L305V/K337A/E296V-FVII.

In a further embodiment of the invention, the factor VII polypeptide is K316H/L305V/K337A/V158D-FVII.

In a further embodiment of the invention, the factor VII polypeptide is K316H/L305V/V158D/M298Q-FVII.

In a further embodiment of the invention, the factor VII polypeptide is K316H/L305V/V158D/E296V-FVII.

In a further embodiment of the invention, the factor VII polypeptide is K316H/L305V/V158T/M298Q-FVII.

In a further embodiment of the invention, the factor VII polypeptide is K316H/L305V/V158T/E296V-FVII.

In a further embodiment of the invention, the factor VII polypeptide is K316H/L305V/E296V/M298Q-FVII.

In a further embodiment of the invention, the factor VII polypeptide is K316H/L305V/V158D/E296V/M298Q-FVII.

In a further embodiment of the invention, the factor VII polypeptide is K316H/L305V/V158T/E296V/M298Q-FVII.

In a further embodiment of the invention, the factor VII polypeptide is K316H/L305V/V158T/K337A/M298Q-FVII.

In a further embodiment of the invention, the factor VII polypeptide is K316H/L305V/V158T/E296V/K337A-FVII.

In a further embodiment of the invention, the factor VII polypeptide is K316H/L305V/V158D/K337A/M298Q-FVII.

In a further embodiment of the invention, the factor VII polypeptide is K316H/L305V/V158D/E296V/K337A-FVII.

In a further embodiment of the invention, the factor VII polypeptide is K316H/L305V/V158D/E296V/M298Q/K337A-FVII.

In a further embodiment of the invention, the factor VII polypeptide is K316H/L305V/V158T/E296V/M298Q/K337A-FVII.

In a further embodiment of the invention, the factor VII polypeptide is K316Q/L305V/K337A-FVII.

In a further embodiment of the invention, the factor VII polypeptide is K316Q/L305V/V158D-FVII.

In a further embodiment of the invention, the factor VII polypeptide is K316Q/L305V/E296V-FVII.

In a further embodiment of the invention, the factor VII polypeptide is K316Q/L305V/M298Q-FVII.

In a further embodiment of the invention, the factor VII polypeptide is K316Q/L305V/V158T-FVII.

In a further embodiment of the invention, the factor VII polypeptide is K316Q/L305V/K337A/V158T-FVII.

In a further embodiment of the invention, the factor VII polypeptide is K316Q/L305V/K337A/M298Q-FVII.

In a further embodiment of the invention, the factor VII polypeptide is K316Q/L305V/K337A/E296V-FVII.

In a further embodiment of the invention, the factor VII polypeptide is K316Q/L305V/K337A/V158D-FVII.

In a further embodiment of the invention, the factor VII polypeptide is K316Q/L305V/V158D/M298Q-FVII.

In a further embodiment of the invention, the factor VII polypeptide is K316Q/L305V/V158D/E296V-FVII.

In a further embodiment of the invention, the factor VII polypeptide is K316Q/L305V/V158T/M298Q-FVII.

In a further embodiment of the invention, the factor VII polypeptide is K316Q/L305V/V158T/E296V-FVII.

In a further embodiment of the invention, the factor VII polypeptide is K316Q/L305V/E296V/M298Q-FVII.

In a further embodiment of the invention, the factor VII polypeptide is K316Q/L305V/V158D/E296V/M298Q-FVII.

In a further embodiment of the invention, the factor VII polypeptide is K316Q/L305V/V158T/E296V/M298Q-FVII.

In a further embodiment of the invention, the factor VII polypeptide is K316Q/L305V/V158T/K337A/M298Q-FVII.

In a further embodiment of the invention, the factor VII polypeptide is K316Q/L305V/V158T/E296V/K337A-FVII.

In a further embodiment of the invention, the factor VII polypeptide is K316Q/L305V/V158D/K337A/M298Q-FVII.

In a further embodiment of the invention, the factor VII polypeptide is K316Q/L305V/V158D/E296V/K337A-FVII.

In a further embodiment of the invention, the factor VII polypeptide is K316Q/L305V/V158D/E296V/M298Q/K337A-FVII.

In a further embodiment of the invention, the factor VII polypeptide is K316Q/L305V/V158T/E296V/M298Q/K337A-FVII.

In a further aspect, the invention provides human coagulation Factor VIIa polypeptides that have increased tissue factor-independent activity compared to native human coagulation Factor VIIa. In another aspect, the increased activity is not accompanied by changes in the substrate specificity. In another aspect of the invention, the binding of the polypeptide variants to tissue factor should not be impaired and the polypeptide variants should have at least the activity of wild-type Factor VIIa when bound to tissue factor.

The terminology for amino acid substitutions used in this description are as follows. The first letter represent the amino acid naturally present at a position of SEQ ID NO:1. The following number represent the position in SEQ ID NO:1. The second letter represent the different amino acid substituting for the natural amino acid. An example is L305V/K337A-FVII, the leucine at position 305 of SEQ ID NO:1 is replaced by a valine and the Lysine at position 337 of SEQ ID NO:1 is replaced by an alanine, both mutations in the same Factor VII polypeptide variant.

In the present context the three-letter or one-letter indications of the amino acids have been used in their conventional meaning as indicated in table 1. Unless indicated explicitly, the amino acids mentioned herein are L-amino acids. Further, the left and right ends of an amino acid sequence of a peptide are, respectively, the N- and C-termini unless otherwise specified.

TABLE 1

| Abbreviations for amino acids: | | |
|---|---|---|
| Amino acid | Tree-letter code | One-letter code |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

Preparation of Factor VII Polypeptide Variants

The invention also relates to a method of preparing human Factor VII polypeptide variants as mentioned above. The Factor VII polypeptide variants described herein may be produced by means of recombinant nucleic acid techniques. In general, a cloned wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known (see U.S. Pat. No. 4,784,950, where the cloning and expression of recombinant human Factor VII is described). The bovine Factor VII sequence is described in Takeya et al., J. Biol. Chem. 263: 14868-14872 (1988)).

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of Factor VII, one may introduce the alteration (s) of choice. Likewise, procedures for preparing a DNA construct using polymerase chain reaction using specific primers are well known to persons skilled in the art (cf. PCR Protocols, 1990, Academic Press, San Diego, Calif., USA).

The polypeptides of the present invention can also comprise non-naturally occurring amino acid residues. Non-naturally occurring amino acids include, without limitation, beta-alanine, desaminohistidine, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

The nucleic acid construct encoding the Factor VII polypeptide variant of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., Molecular Cloning: A Laboratory Manual, 2nd. Ed. Cold Spring Harbor Laboratory, Cold Spring Harbor, N.Y., 1989).

The nucleic acid construct encoding the Factor VII polypeptide variant may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesised, e.g. in an automatic DNA synthesiser, purified, annealed, ligated and cloned in suitable vectors. The DNA sequences encoding the human Factor VII polypeptide variants may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct. DNA sequences for use in producing Factor VII polypeptide variants according to the present invention will typically encode a pre-pro polypeptide at the amino-terminus of Factor VII to obtain proper posttranslational processing (e.g. gamma-carboxylation of glutamic acid residues) and secretion from the host cell. The pre-pro polypeptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the Factor VII polypeptide variants where those modifications do not significantly impair the ability of the protein to act as a coagulant. For example, the Factor VII polypeptide variants can also be modified in the activation cleavage site to inhibit the conversion of zymogen Factor VII into its activated two-chain form, as generally described in U.S. Pat. No. 5,288,629, incorporated herein by reference.

The DNA sequences encoding the human Factor VII polypeptide variants are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Factor VII polypeptide variants is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors for use in expressing Factor VIIa polypeptide variants will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Factor VII polypeptide variant in mammalian cells are the SV40 promoter (Subramani et al., *Mol. Cell Biol.* 1 (1981), 854-864), the MT-1 (metallothionein gene) promoter (Palmiter et al., *Science* 222 (1983), 809-814), the CMV promoter (Boshart et al., *Cell* 41:521-530, 1985) or the adenovirus 2 major late promoter (Kaufman and Sharp, *Mol. Cell. Biol,* 2:1304-1319, 1982).

An example of a suitable promoter for use in insect cells is the polyhedrin promoter (U.S. Pat. No. 4,745,051; Vasuvedan et al., *FEBS Lett.* 311, (1992) 7-11), the P10 promoter (J. M. Vlak et al., *J. Gen. Virology* 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073-12080; Alber and Kawasaki, *J. Mol. Appl. Gen.* 1 (1982), 419-434) or alcohol dehydrogenase genes (Young et al., in *Genetic Engineering of*

*Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652-654) promoters.

Examples of suitable promoters for use in filamentous fungus host cells are, for instance, the ADH3 promoter (McKnight et al., *The EMBO J.* 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the human Factor VII polypeptide variants may also, if necessary, be operably connected to a suitable terminator, such as the human growth hormone terminator (Palmiter et al., *Science* 222, 1983, pp. 809-814) or the TPI1 (Alber and Kawasaki, *J. Mol. Appl. Gen.* 1, 1982, pp. 419-434) or ADH3 (McKnight et al., *The EMBO J.* 4, 1985, pp. 2093-2099) terminators. Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

To direct the human Factor VII polypeptide variants of the present invention into the secretory pathway of the host cells, a secretory signal sequence (also known as a leader sequence, prepro sequence or pre sequence) may be provided in the recombinant vector. The secretory signal sequence is joined to the DNA sequences encoding the human Factor VII polypeptide variants in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed human Factor VII polypeptide variants into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643-646), a modified carboxypeptidase signal peptide (cf. L.A. Valls et al., *Cell* 48, 1987, pp. 887-897), the yeast BAR1 signal peptide (cf. WO 87/02670), or the yeast aspartic protease 3 (YAP3) signal peptide (cf. M. Egel-Mitani et al., *Yeast* 6, 1990, pp. 127-137).

For efficient secretion in yeast, a sequence encoding a leader peptide may also be inserted downstream of the signal sequence and upstream of the DNA sequence encoding the human Factor VII polypeptide variants. The function of the leader peptide is to allow the expressed peptide to be directed from the endoplasmic reticulum to the Golgi apparatus and further to a secretory vesicle for secretion into the culture medium (i.e. exportation of the human Factor VII polypeptide variants across the cell wall or at least through the cellular membrane into the periplasmic space of the yeast cell). The leader peptide may be the yeast alpha-factor leader (the use of which is described in e.g. U.S. Pat. No. 4,546,082, U.S. Pat. No. 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the human Factor VII polypeptide variants, the promoter and optionally the terminator and/or secretory signal sequence, respectively, and to insert them into suitable vectors containing the information necessary for replication, are well known to persons skilled in the art (cf., for instance, Sambrook et al., *Molecular Cloning: A Laboratory Manual*, Cold Spring Harbor, N.Y., 1989).

Methods of transfecting mammalian cells and expressing DNA sequences introduced in the cells are described in e.g. Kaufman and Sharp, *J. Mol. Biol.* 159 (1982), 601-621; Southern and Berg, *J. Mol. Appl. Genet.* 1 (1982), 327-341; Loyter et al., *Proc. Natl. Acad. Sci. USA* 79 (1982), 422-426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (Mammalian Cell Technology, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If, on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the human Factor VII polypeptide variants of interest. Media generally include a carbon source, a nitrogen source, essential amino acids, essential sugars, vitamins, salts, phospholipids, protein and growth factors. For production of gamma-carboxylated proteins, the medium will contain vitamin K, preferably at a concentration of about 0.1 µg/ml to about 5 µg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the human Factor VII polypeptide variant of interest.

The host cell into which the DNA sequences encoding the human Factor VII polypeptide variants is introduced may be any cell, which is capable of producing the posttranslational modified human Factor VII polypeptide variants and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982, incorporated herein by reference), hereinafter referred to as BHK 570 cells. The BHK 570 cell line has been deposited with the American Type Culture Collection, 10801 University Boulevard, Manassas, Va. 20110, under ATCC accession number CRL 10314. A tk– ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, *Proc. Natl. Acad. Sci. USA* 77:4216-4220, 1980).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous polypeptides there from are described, e.g. in U.S. Pat. No. 4,599,311, U.S. Pat. No. 4,931,373, U.S. Pat. Nos. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the human Factor VII polypeptide variants may be preceded by a signal sequence and optionally a leader sequence, e.g. as described above. Further examples of suitable yeast cells are strains of *Kluyveromyces*, such as *K. lactis*, *Hansenula*, e.g. *H. polymorpha*, or *Pichia*, e.g. *P. pastoris* (cf. Gleeson et al., *J. Gen. Microbiol.* 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae*, *A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, *Gene* 78:147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. No. 4,745,051; U.S. Pat. No. 4,879,236; U.S. Pat. Nos. 5,155,037; 5,162,222; EP 397,485) all of which are incorporated herein by reference. The insect cell line used as the host may suitably be a *Lepidoptera* cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the human Factor VII polypeptide variant after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The human Factor VII polypeptide variant produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

Transgenic animal technology may be employed to produce the Factor VII polypeptide variants of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene (see Whitelaw et al., Biochem. J. 286: 31-39 (1992)). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836-840 (1988); Palmiter et al., Proc. Natl. Acad. Sci. USA 88: 478-482 (1991); Whitelaw et al., Transgenic Res. 1: 3-13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment that provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the variant Factor VII sequence is replaced with corresponding sequences from a milk specific protein gene. Such replacement provides a putative tissue-specific initiation environment to enhance expression. It is convenient to replace the entire variant Factor VII pre-pro and 5' non-coding sequences with those of, for example, the BLG gene, although smaller regions may be replaced.

For expression of Factor VII polypeptide variants in transgenic animals, a DNA segment encoding variant Factor VII is operably linked to additional DNA segments required for its expression to produce expression units. Such additional segments include the above-mentioned promoter, as well as sequences that provide for termination of transcription and polyadenylation of mRNA. The expression units will further include a DNA segment encoding a secretory signal sequence operably linked to the segment encoding modified Factor VII. The secretory signal sequence may be a native Factor VII secretory signal sequence or may be that of another protein, such as a milk protein (see, for example, von Heijne, Nucl. Acids Res. 14: 4683-4690 (1986); and Meade et al., U.S. Pat. No. 4,873,316, which are incorporated herein by reference).

Construction of expression units for use in transgenic animals is conveniently carried out by inserting a variant Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a Factor VII variant; thereby creating a gene fusion that includes the expression control sequences of the milk protein gene. In any event, cloning of the expression units in plasmids or other vectors facilitates the amplification of the variant Factor VII sequence. Amplification is conveniently carried out in bacterial (e.g. *E. coli*) host cells, thus the vectors will typically include an origin of replication and a selectable marker functional in bacterial host cells. The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, Science 240: 1468-1474 (1988)) or site-directed integration using embryonic stem (ES) cells (reviewed by Bradley et al., Bio/Technology 10: 534-539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179-183 (1988); Wall et al., Biol. Reprod. 32: 645-651 (1985); Buhler et al., Bio/Technology 8: 140-143 (1990); Ebert et al., Bio/Technology 9: 835-838 (1991); Krimpenfort et al., Bio/Technology 9: 844-847 (1991); Wall et al., J. Cell. Biochem. 49:113-120 (1992); U.S. Pat. No. 4,873,191; U.S. Pat. No. 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380-7384 (1980); Gordon and Ruddle, Science 214: 1244-1246 (1981); Palmiter and Brinster, Cell 41: 343-345 (1985); Brinster et al., Proc. Natl. Acad. Sci. USA 82: 4438-4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179-183 (1988)). To summarise, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, Nature 344:469-479 (1990); Edelbaum et al., J. Interferon Res. 12:449-453 (1992); Sijmons et al., Bio/Technology 8:217-221 (1990); and EP 0 255 378).

The Factor VII polypeptide variants of the invention are recovered from cell culture medium or milk. The Factor VII polypeptide variants of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, N.Y., 1989). Preferably, they may be purified by affinity chromatography on an anti-Factor VII antibody column. The use of calcium-dependent monoclonal antibodies, as described by Wakabayashi et al., J. Biol. Chem. 261:11097-11108, (1986) and Thim et al., Biochemistry 27: 7785-7793, (1988), is particularly preferred. Additional purification may be achieved by conventional chemical purification means, such as high performance liquid chromatography. Other methods of purification, including barium citrate precipitation, are known in the art, and may be applied to the purification of the novel Factor VII polypeptide variants described herein (see, for example, Scopes, R., Protein Purification, Springer-Verlag, N.Y., 1982).

For therapeutic purposes it is preferred that the Factor VII polypeptide variants of the invention are substantially pure. Thus, in a preferred embodiment of the invention the Factor VII polypeptide variants of the invention is purified to at least about 90 to 95% homogeneity, preferably to at least about 98% homogeneity. Purity may be assessed by e.g. gel electrophoresis and amino-terminal amino acid sequencing.

The Factor VII variant is cleaved at its activation site in order to convert it to its two-chain form. Activation may be carried out according to procedures known in the art, such as those disclosed by Osterud, et al., Biochemistry 11:2853-2857 (1972); Thomas, U.S. Pat. No. 4,456,591; Hedner and Kisiel, J. Clin. Invest. 71:1836-1841 (1983); or Kisiel and Fuji-kawa, Behring Inst. Mitt. 73:29-42 (1983). Alternatively, as described by Bjoern et al. (Research Disclosure, 269 Sep. 1986, pp. 564-565), Factor VII may be activated by passing it through an ion-exchange chromatography column, such as MONO Q® (Pharmacia fine Chemicals) or the like. The resulting activated Factor VII variant may then be formulated and administered as described below.

Assays

The invention also provides suitable assays for selecting preferred Factor VIIa variants according to the invention. These assays can be performed as a simple preliminary in vitro test.

Thus, Example 4 herein discloses a simple test (entitled "In Vitro Hydrolysis Assay") for the activity of Factor VIIa variants of the invention. Based thereon, Factor VIIa variants which are of particular interest are such variants where the ratio between the activity of the variant and the activity of native Factor VII shown in FIG. 1 is above 1.0, e.g. at least about 1.25, preferably at least about 2.0, such as at least about 3.0 or, even more preferred, at least about 4.0 when tested in the "In Vitro Hydrolysis Assay".

The activity of the variants can also be measured using a physiological substrate such as factor X ("In Vitro Proteolysis Assay") (see Example 5), suitably at a concentration of 100-1000 nM, where the factor Xa generated is measured after the addition of a suitable chromogenic substrate (eg. S-2765). In addition, the activity assay may be run at physiological temperature.

The ability of the Factor VIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547 which is hereby incorporated as reference).

Administration and Pharmaceutical Compositions

The Factor VII polypeptide variants according to the present invention may be used to control bleeding disorders which have several causes such as clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or vast trauma, the haemostatic mechanism may be overwhelmed by the demand of immediate haemostasis and they may develop bleedings in spite of a normal haemostatic mechanism. Achieving satisfactory haemostasis is also a problem when bleedings occur in organs such as the brain, inner ear region and eyes and may also be a problem in cases of diffuse bleedings (haemorrhagic gastritis and profuse uterine bleeding) when it is difficult to identify the source. The same problem may arise in the process of taking biopsies from various organs (liver, lung, tumour tissue, gastrointestinal tract) as well as in laparoscopic surgery. These situations share the difficulty of providing haemostasis by surgical techniques (sutures, clips, etc.). Acute and profuse bleedings may also occur in subjects on anticoagulant therapy in whom a defective haemostasis has been induced by the therapy given. Such subjects may need surgical interventions in case the anticoagulant effect has to be counteracted rapidly. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

A systemic activation of the coagulation cascade may lead to disseminated intravascular coagulation (DIC). However, such complications have not been seen in subjects treated with high doses of recombinant Factor VIIa because of a localised haemostatic process of the kind induced by the complex formation between Factor VIIa and TF exposed at the site of vessel wall injury. The Factor VII polypeptide variants according to the invention may thus also be used in their activated form to control such excessive bleedings associated with a normal haemostatic mechanism.

For treatment in connection with deliberate interventions, the Factor VII polypeptide variants of the invention will typically be administered within about 24 hours prior to performing the intervention, and for as much as 7 days or more thereafter. Administration as a coagulant can be by a variety of routes as described herein.

The dose of the Factor VII polypeptide variants ranges from about 0.05 mg to 500 mg/day, preferably from about 1 mg to 200 mg/day, and more preferably from about 10 mg to about 175 mg/day for a 70 kg subject as loading and maintenance doses, depending on the weight of the subject and the severity of the condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII variant of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII polypeptide variants of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII variant in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion can be made up to contain 250 ml of sterile Ringer's solution and 10 mg of the Factor VII variant. Actual methods for preparing parenterally administrable compositions will be known or apparent to those skilled in the art and are described in more detail in, for example, Remington's Pharmaceutical Sciences, 18th ed., Mack Publishing Company, Easton, Pa. (1990).

The compositions containing the Factor VII polypeptide variants of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective amount will range from about 0.05 mg up to about 500 mg of the Factor VII variant per day for a 70 kg subject, with dosages of from about 1.0 mg to about 200 mg of the Factor VII variant per day being more commonly used.

The FVIIa polypeptides of the present invention may generally be employed in serious disease or injury states, that is, life threatening or potentially life threatening situations. In such cases, in view of the minimisation of extraneous substances and general lack of immunogenicity of human Factor VII polypeptide variants in humans, it may be felt desirable by the treating physician to administer a substantial excess of these variant Factor VII compositions.

In prophylactic applications, compositions containing the Factor VII variant of the invention are administered to a subject susceptible to or otherwise at risk of a disease state or injury to enhance the subject's own coagulative capability. Such an amount is defined to be a "prophylactically effective dose". In prophylactic applications, the precise amounts once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Factor VII polypeptide variants may be administered by continuous infusion using e.g. a portable pump system.

Local delivery of the Factor VII variant of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII variant sufficient to effectively treat the subject.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

The terminology for amino acid substitutions used in the following examples are as follows. The first letter represent the amino acid naturally present at a position of SEQ ID NO:1. The following number represent the position in SEQ ID NO:1. The second letter represent the different amino acid substituting for the natural amino acid. An example is S314E/K316H-FVII, the serine at position 314 of SEQ ID NO:1 is replaced by a glutamic acid and the Lysine at position 316 of SEQ ID NO:1 is replaced by a histidine, both mutations in the same Factor VII variant.

Example 1

DNA Encoding S314E-FVII, S314E/K316H-FVII and S314E/K316Q-FVII.

DNA constructs encoding S314E/K316H-FVII and S314E/K316Q-FVII were prepared by site-directed mutagenesis using a supercoiled, double stranded DNA vector with an insert of interest and two synthetic primers containing the desired mutation. The following primers were used:

```
(DNA primer for preparation of S314E/K316H-FVII):
                                                    SEQ ID NO:2
5'-CTG CCT GCA GCA GGA ACG GCA CGT GGG AGA CTC CCC-3'

(DNA primer for preparation of S314E/K316H FVII):-
                                                    SEQ ID NO:3
```

```
                          -continued
5'-GGG GAG TCT CCC ACG TGC CGT TCC TGC TGC AGG CAG-3'

(DNA primer for preparation of S314E/K316Q-FVII):
                                              SEQ ID NO:4
5'-CCT GCA GCA GGA ACG GCA GGT GGG AGA CTC CCC-3'

(DNA primer for preparation of S314E/K316Q-FVII):
                                              SEQ ID NO:5
5'-GGG GAG TCT CCC ACC TGC CGT TCC TGC TGC AGG-3'

(DNA primer for preparation of S314E-FVII):
                                              SEQ ID NO:6
5'-GCC TGC AGC AGG AAC GGA AGG TGG GAG ACT CC-3'

(DNA primer for preparation of S314E-FVII):
                                              SEQ ID NO:7
5'-GGA GTC TCC CAC CTT CCG TTC CTG CTG CAG GC-3'
```

The oligonucleotide primers, each complementary to opposite strands of the vector, were extended during temperature cycling by means of Pfu DNA polymerase. On incorporation of the primers, a mutated plasmid containing staggered nicks was generated. Following temperature cycling, the product was treated with Dpnl which is specific for methylated and hemimethylated DNA to digest the parental DNA template and to select for mutation-containing synthesized DNA.

Procedures for preparing a DNA construct using polymerase chain reaction using specific primers are well known to persons skilled in the art (cf. PCR Protocols, 1990, Academic Press, San Diego, Calif., USA).

Example 2

Preparation of S314E/K316H-FVII.

BHK cells were transfected essentially as previously described (Thim et al. (1988) Biochemistry 27, 7785-7793; Persson and Nielsen (1996) FEBS Lett. 385, 241-243) to obtain expression of the variant S314E/K316H-FVII. The Factor VII variant was purified as follows:

Conditioned medium was loaded onto a 25-ml column of Q Sepharose Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water.

Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100® pH 8.0. The fractions containing S314E/K316H-FVII were pooled and applied to a 25-ml column containing monoclonal antibody F1A2 (Novo Nordisk, Bagsvaerd, Denmark) coupled to CNBr-activated Sepharose 4B (Pharmacia Biotech).

The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or S314E/K316H-FVII was transferred to a $Ca^{2+}$-containing buffer. The yield of each step was followed by factor VII ELISA measurements and the purified protein was analysed by SDS-PAGE.

Example 3

Preparation of S314E/K316Q-FVII.

BHK cells were transfected essentially as previously described (Thim et al. (1988) Biochemistry 27, 7785-7793; Persson and Nielsen (1996) FEBS Lett. 385, 241-243) to obtain expression of the variant S314E/K316Q-FVII. The Factor VII variant was purified as follows:

Conditioned medium was loaded onto a 25-ml column of Q Sepharose Fast Flow (Pharmacia Biotech) after addition of 5 mM EDTA, 0.1% TRITON X-100® and 10 mM Tris, adjustment of pH to 8.0 and adjustment of the conductivity to 10-11 mS/cm by adding water. Elution of the protein was accomplished by stepping from 10 mM Tris, 50 mM NaCl, 0.1% TRITON X-100®, pH 8.0 to 10 mM Tris, 50 mM NaCl, 25 mM $CaCl_2$, 0.1% TRITON X-100®, pH 8.0. The fractions containing S314E/K316Q-FVII were pooled and applied to a 25-ml column containing monoclonal antibody F1A2 (Novo Nordisk, Bagsvaerd, Denmark) coupled to CNBr-activated Sepharose 4B (Pharmacia Biotech).

The column was equilibrated with 50 mM Hepes, pH 7.5, containing 10 mM $CaCl_2$, 100 mM NaCl and 0.02% TRITON X-100®. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or S314E/K316Q-FVII was transferred to a $Ca^{2+}$-containing buffer. The yield of each step was followed by factor VII ELISA measurements and the purified protein was analysed by SDS-PAGE.

All other Factor VII polypeptide according to the present invention may be prepared with specific primers known to the person skilled in the art, by the same procedure as described in the previous examples.

Example 4

In Vitro Hydrolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\,nm}$ Factor VIIa variant)/($A_{405\,nm}$ Factor VIIa wild-type).

Example 5

In Vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A_{405\,nm}$ Factor VIIa variant)/($A_{405\,nm}$ Factor VIIa wild-type).

Example 6

RELATIVE ACTIVITIES OF FVIIA VARIANTS MEASURED IN THE ASSAYS DESCRIBED IN EXAMPLES 4 AND 5.

| Variant | Ratio in example 4 | Ratio in example 5 |
|---|---|---|
| S314E-FVIIa | 2.6 | 1.5 |
| S314E/K316Q-FVIIa | 2.8 | 1.2 |
| S314E/K316H-FVIIa | 2.9 | 0.8 |
| Wt-FVIIa | 1.0 | 1.0 |

The invention claimed is:

1. An isolated polynucleotide construct encoding a Factor VII variant polypeptide comprising at least one amino acid substitution selected from the group consisting of amino acids 313, 314, 317-329, 364, 366, 373, and 376 of SEQ ID NO:1, wherein the ratio between the activity of said Factor VII variant polypeptide and the activity of a native Factor VIIa polypeptide is at least 1.25, when the activity is measured in an in vitro hydrolysis assay.

2. The polynucleotide construct as defined in claim 1, wherein said construct encodes a polypeptide in which S314 is replaced with any other amino acid.

3. The polynucleotide construct as defined in claim 1, wherein said construct encodes a Factor VII variant polypeptide further comprising at the most 20 additional amino acids in the remaining positions within residues 153-406 of SEQ ID NO:1, each of said residues being replaced with any other amino acid.

4. The polynucleotide construct as defined in claim 3, wherein said construct encodes a polypeptide in which at least one amino acid corresponding to an amino acid at a position selected from 330-339 of SEQ ID NO:1 has been replaced with any other amino acid.

5. The polynucleotide construct as defined in claim 4, wherein the additional replacement comprises replacement of one or more amino acids selected from the group consisting of amino acids L305, K157, K337, D334, S336, V158, E296, and M298 of SEQ ID NO:1.

6. The polynucleotide construct as defined in claim 1, wherein said construct encodes a polypeptide in which S314 has been replaced by an amino acid selected from the group consisting of Gly and Glu.

7. The polynucleotide construct as defined in claim 1, wherein said S314 has been replaced by Glu.

8. The polynucleotide construct as defined in claim 1, wherein said polypeptide further comprises replacement of K316 by Gln.

9. The polynucleotide construct as defined in claim 1, wherein the polypeptide is selected from the group consisting of S314E/K316H-FVII and S314E/K316Q-FVII.

10. The polynucleotide as defined in claim 1, wherein said construct is a vector.

11. An isolated host cell comprising a polynucleotide construct as defined in claim 10.

12. The host cell as defined in claim 11, wherein said cell is a eukaryotic cell.

13. The host cell as defined in claim 12, wherein said cell is of mammalian origin.

14. The host cell as defined in claim 13, wherein the cell is selected from the group consisting of CHO cells, HEK cells, and BHK cells.

15. A method for producing a Factor VII polypeptide, the method comprising (i) cultivating a cell as defined in claim 11, in an appropriate growth medium under conditions allowing expression of the polynucleotide construct and (ii) recovering the resulting polypeptide from the culture.

* * * * *

```
SEQUENCE LISTING

<160> NUMBER OF SEQ ID NOS: 7

<210> SEQ ID NO 1
<211> LENGTH: 406
<212> TYPE: PRT
<213> ORGANISM: Homo Sapiens
<220> FEATURE:
<223> OTHER INFORMATION: Xaa means 4-carboxyglutamic acid
      (gamma-carboxyglutamate)

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175
```

-continued

```
Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
            195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
            275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
            355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 2
<211> LENGTH: 36
<212> TYPE: DNA
<213> ORGANISM: Unknown
<220> FEATURE:
<223> OTHER INFORMATION: DNA primer for preparation of S314E/K316H-FVII

<400> SEQUENCE: 2
ctgcctgcag caggaacggc acgtgggaga ctcccc                              36

<210> SEQ ID NO 3
<211> LENGTH: 36
<212> TYPE: DNA
<213> ORGANISM: Unknown
<220> FEATURE:
<223> OTHER INFORMATION: DNA primer for preparation of S314E/K316H-FVII

<400> SEQUENCE: 3
ggggagtctc ccacgtgccg ttcctgctgc aggcag                              36

<210> SEQ ID NO 4
<211> LENGTH: 33
<212> TYPE: DNA
<213> ORGANISM: Unknown
<220> FEATURE:
<223> OTHER INFORMATION: DNA primer for preparation of S314E/K316Q-FVII

<400> SEQUENCE: 4
```

```
cctgcagcag gaacggcagg tgggagactc ccc                                         33
```

<210> SEQ ID NO 5
<211> LENGTH: 33
<212> TYPE: DNA
<213> ORGANISM: Unknown
<220> FEATURE:
<223> OTHER INFORMATION: DNA primer for preparation of S314E/K316Q-FVII

<400> SEQUENCE: 5

```
ggggagtctc ccacctgccg ttcctgctgc agg                                         33
```

<210> SEQ ID NO 6
<211> LENGTH: 32
<212> TYPE: DNA
<213> ORGANISM: Unknown
<220> FEATURE:
<223> OTHER INFORMATION: DNA primer for preparation of S314E-FVII

<400> SEQUENCE: 6

```
gcctgcagca ggaacggaag gtgggagact cc                                          32
```

<210> SEQ ID NO 7
<211> LENGTH: 32
<212> TYPE: DNA
<213> ORGANISM: Unknown
<220> FEATURE:
<223> OTHER INFORMATION: DNA primer for preparation of S314E-FVII

<400> SEQUENCE: 7

```
ggagtctccc accttccgtt cctgctgcag gc                                          32
```